United States Patent [19]

Lam

[11] 4,303,792

[45] Dec. 1, 1981

[54] N-SUBSTITUTED HALOACYLOXYACETAMIDES HERBICIDAL ANTIDOTES

[75] Inventor: Hsaio-Ling Lam, Walnut Creek, Calif.

[73] Assignee: Stauffer Chemical Company, Westport, Conn.

[21] Appl. No.: 42,187

[22] Filed: May 24, 1979

[51] Int. Cl.³ .................. A01N 43/76; A01N 37/18; C07D 263/06; C07C 69/63
[52] U.S. Cl. .................. 548/215; 71/88; 106/900; 560/226
[58] Field of Search .................. 260/307 FA; 548/215

[56] References Cited

U.S. PATENT DOCUMENTS

| | | | |
|---|---|---|---|
| 2,913,377 | 11/1959 | Tilles | 71/2.7 |
| 3,884,671 | 5/1975 | Albright et al. | 548/215 |
| 4,021,224 | 5/1977 | Pallos | 71/88 |

*Primary Examiner*—Anton H. Sutto
*Attorney, Agent, or Firm*—Harry A. Pacini

[57] ABSTRACT

N-substituted haloacyloxyacetamide compounds having the following formula:

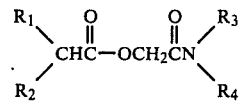

in which $R_1$ is selected from the group consisting of chlorine and bromomethyl;

$R_2$ is selected from the group consisting of hydrogen, chlorine and bromine;

$R_3$ is selected from the group consisting of hydrogen, 1-4 carbon alkyl, 2-10 carbon alkenyl, and methylene malononitrile;

$R_4$ is selected from the group consisting of 1-10 carbon alkyl, 2-10 carbon alkenyl, 2-10 carbon alkynyl, and substituted phenyl wherein said substituents are chloro or 1-6 chloro alkyl; or $R_3$ and $R_4$ together with the nitrogen atom to which they are attached are selected from the group consisting of 4-10 carbon alkylene ring and 4-10 carbon alkyl substituted oxazolidine ring; provided that when $R_1$ and $R_2$ are chlorine, then $R_3$ and $R_4$ are other than allyl. The compounds are useful as herbicidal antidotes for protection of crops from thiocarbamate herbicidal injury.

6 Claims, No Drawings

N-SUBSTITUTED HALOACYLOXYACETAMIDES HERBICIDAL ANTIDOTES

BACKGROUND OF THE INVENTION

Uses of Herbicides

An herbicide is a compound which controls or modifies plant growth, e.g., killing, retarding, defoliating, desiccating, regulating, stunting, tillering, stimulating, and dwarfing. "Plant" refers to all physical parts, including seeds, seedlings, saplings, roots, tubers, stems, stalks, foliage, and fruits. "Plant growth" is meant to include all phases of development from seed germination to natural or induced cessation of life.

Herbicides are generally used to control or eradicate weed pests. They have gained a high degree of commercial success because it has been shown that such control increases crop yield and reduces harvesting costs.

Herbicidal effectiveness is dependent upon several variables. One of these is the time or growth related method of application. The most popular methods of application include: pre-plant incorporation into the soil; pre-emergence surface treatment of seeded soil; and post-emergence treatment of the plant and soil.

The most important determinant of herbicidal effectiveness is the susceptibility of the target weed pest. Certain herbicidal compounds are phytotoxic to some weed species but not to others.

The manufacturer of the herbicide recommends a range of rates and concentrations calculated to maximize weed control. The range of rates varies from approximately 0.01 to 50 pounds per acre (lb/A) (0.0112 to 56 kilograms per hectare (k/ha)), usually from 0.1 to 25 lb/A (0.112 to 28 k/ha). The actual amount used depends upon several considerations including particular weed susceptibility and overall cost limitations.

Need for Herbicidal Antidotes

Unfortunately, few herbicides are selective exclusively of weed species. Many are toxic to both weeds and the intended crop beneficiary. Therefore, a particular herbicide's use may be proscribed by its injurious effect on the cultivated crop even though it may otherwise provide excellent control of weeds plaguing that crop.

To preserve the beneficial aspects of herbicide use and to mitigate crop damage, many herbicidal antidotes have been prepared. These antidotes reduce or eliminate damage to the crop without substantially impairing the ameliorative effect of the herbicide. See U.S. Pat. No. 4,021,224 and Belgian Pat. 846,894.

Although several explanatory theories have been advanced, the precise mechanism by which an antidote reduces herbicidal injury has not been empirically verified. An antidote compound may in fact be a remedy, interferent, protectant, or antagonist. As used herein "antidote" describes the effect of herbicidal phytotoxicity to weed species and reduced or non-phytotoxicity to cultivated crop species.

DESCRIPTION OF THE INVENTION

Thiocarbamate herbicides correspond to the following general formula:

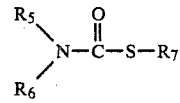

in which
- $R_5$ is selected from the group consisting of 1–6 carbon alkyl, 2–6 carbon alkenyl, and 2–6 carbon alkynyl;
- $R_6$ is selected from the group consisting of 1–6 carbon alkyl, 2–6 carbon alkenyl, cyclohexyl and phenyl; or
- $R_5$ and $R_6$ taken together with the nitrogen atom to which they are attached form an alkylene ring; and
- $R_7$ is selected from the group consisting of 1–6 carbon alkyl, 1–6 carbon haloalkyl, 5–10 carbon alkylene ring, phenyl, substituted phenyl, benzyl, and substituted benzyl. See U.S. Pat. Nos. 2,913,327; 3,198,786; 3,185,720; 2,913,324; and 3,846,115.

The thiocarbamates have been shown particularly effective in the control of grassy type weeds which interfere with the production of a wide variety of crops, e.g., barley, corn, lentils, peanuts, peas, potatoes, soybeans, spinach, tobacco and tomatoes.

It has been discovered that the tolerances of cultivated crop plants to these herbicides can be increased. This can be accomplished by the use of an antidotally effective amount of a compound from the N-substituted haloacyloxyacetamide family corresponding to the following formula:

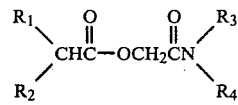

in which
- $R_1$ is selected from the group consisting of chlorine and bromomethyl;
- $R_2$ is selected from the group consisting of hydrogen, chlorine and bromine;
- $R_3$ is selected from the group consisting of hydrogen, 1–4 carbon alkyl, 2–10 carbon alkenyl which is preferably allyl, and methylene malononitrile;
- $R_4$ is selected from the group consisting of 1–10, preferably 1–5, carbon alkyl, 2–10 carbon alkenyl which is preferably allyl, 2–10, preferably 2–5, carbon alkynyl, and substituted phenyl wherein said substituent is chloro or 1–6 carbon alkyl; or
- $R_3$ and $R_4$ together with the nitrogen atom to which they are attached are selected from the group consisting of 4–10 carbon alkylene ring and 4–10 carbon alkyl substituted oxazolidine ring; provided that when $R_1$ and $R_2$ are chlorine, then $R_3$ and $R_4$ are other than allyl.

This invention also embodies a two-part herbicidal system comprised of
(a) an antidotally effective amount of an N-substituted haloacyloxyacetamide of the formula

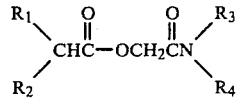

in which

R₁ is selected from the group consisting of chlorine and bromomethyl;

R₂ is selected from the group consisting of hydrogen, chlorine and bromine;

R₃ is selected from the group consisting of hydrogen, 1-4 carbon alkyl, 2-10 carbon alkenyl which is preferably allyl, and methylene malononitrile;

R₄ is selected from the group consisting of 1-10, preferably 1-5, carbon alkyl, 2-10 carbon alkenyl which is preferably allyl, 2-10, preferably 2-5, carbon alkynyl, and substituted phenyl wherein said substituent is chloro or 1-6 carbon alkyl; or R₃ and R₄ together with the nitrogen atom to which they are attached are selected from the group consisting of 4-10 carbon alkylene ring and 4-10 carbon alkyl substituted oxazolidine ring; provided that when R₁ and R₂ are chlorine, then R₃ and R₄ are other than allyl; and (b) an herbicidally effective amount of a thiocarbamate of the formula

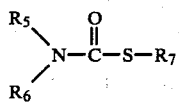

in which

R₅ is selected from the group consisting of 1-6 carbon alkyl and 2-6 carbon alkenyl;

R₆ is selected from the group consisting of 1-6 carbon alkyl and 2-6 carbon alkenyl, 2-6 carbon alkynyl, cyclohexyl and phenyl; or R₅ and R₆ taken together with the nitrogen atom to which they are attached form an alkylene ring; and R₇ is selected from the group consisting of 1-6 carbon alkyl, 1-6 carbon haloalkyl, 5-10 carbon alkylene ring, phenyl, substituted phenyl, benzyl and substituted benzyl.

The antidote compound of this composition may comprise between approximately 0.001 to 30 parts by weight per part of the thiocarbamate herbicide.

This herbicidal system has been shown to be particularly effective for the control of grassy type weeds such as watergrass (*Echinochloa crusgalli*), foxtail (*Setaria viridis*), wild oat (*Avena fatua*), yellow nutsedge (*Cyperus esculentus*), and Johnsongrass (*Sorghum halepense*), while substantially reducing the injury to the cultivated crop species.

The present invention includes the method of controlling undesirable vegetation while reducing herbicidal injury by adding to the soil an antidote compound from the N-substituted haloacyloxyacetamide family corresponding to the following formula:

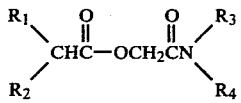

in which

R₁ is selected from the group consisting of chlorine and bromomethyl;

R₂ is selected from the group consisting of hydrogen, chlorine and bromine;

R₃ is selected from the group consisting of hydrogen, 1-4 carbon alkyl, 2-10 carbon alkenyl which is preferably allyl, and methylene malononitrile;

R₄ is selected from the group consisting of 1-10, preferably 1-5, carbon alkyl, 2-10 carbon alkenyl which is preferably allyl, 2-10, preferably 2-5, carbon alkynyl, and substituted phenyl wherein said substituent is chloro or 1-6 carbon alkyl; or R₃ and R₄ together with the nitrogen atom to which they are attached are selected from the group consisting of 4-10 carbon alkylene ring and 4-10 carbon alkyl substituted oxazolidine ring; provided that when R₁ and R₂ are chlorine, then R₃ and R₄ are other than allyl.

The antidote may be combined with the herbicide in a tank mix by pre-plant incorporation (PPI). It may be applied by the in-furrow (IF) surface spray of seeds and soil before the seeds are covered with soil. It may also be applied by seed treatment (ST) which consists of combining in a suitable container 10 grams of the seed and 0.5 ml of antidote stock solution. Pre-emergent (PES) methods of application to the seeded soil are also possible, but less effective with the compounds and compositions of this invention than PPI or IF methods.

This invention also includes soil treated with the herbicidal system comprised of a thiocarbamate herbicide and a compound having the following formula:

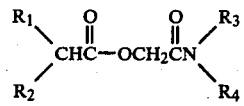

in which

R₁ is selected from the group consisting of chlorine and bromomethyl;

R₂ is selected from the group consisting of hydrogen, chlorine and bromine;

R₃ is selected from the group consisting of hydrogen, 1-4 carbon alkyl, 2-10 carbon alkenyl which is preferably allyl, and methylene malononitrile;

R₄ is selected from the group consisting of 1-10, preferably 1-5, carbon alkyl, 2-10 carbon alkenyl which is preferably allyl, 2-10, preferably 2-5, carbon alkynyl, and substituted phenyl wherein said substituent is chloro or 1-6 carbon alkyl; or R₃ and R₄ together with the nitrogen atom to which they are attached are selected from the group consisting of 4-10 carbon alkylene ring and 4-10 carbon alkyl substituted oxazolidine ring; provided that when R₁ and R₂ are chlorine, then R₃ and R₄ are other than allyl.

PREPARATION

The thiocarbamates of the present compositions can be prepared by the procedures described in the commonly assigned and expired U.S. Pat. No. 2,913,327.

The compounds of this invention represented by the above formula can be prepared by several different procedures depending upon the starting materials. The following procedure is a general method of preparation.

An acid chloride and a suitable amine are separately dissolved in the same non-reactive solvent, such as methylene chloride or tetrahydrofuran. Keeping all reactants in equimolar amounts, either the acid chloride is slowly added to the amine in the presence of an acid acceptor such as a tertiary amine, or the two amines are added to the acid chloride. The mixture is cooled in an ice bath during addition. The reaction takes place over several hours at temperatures ranging from −40° C. to +40° C. The reaction product is water washed and dried with magnesium sulfate. The solvent is evaporated under reduced pressure.

A second general method of preparation follows the above procedure but uses a glycolamide as a reactant rather than an amine.

Table I lists the compounds which were prepared according to one of these general methods.

The following examples illustrate the specific preparation of the compounds typical of this invention. (The compound numbers correspond to those appearing in Tables I, II, and III.)

EXAMPLE 1

Preparation of N-methyl dichloroacetoxyacetamide (Compound No. 2)

A solution was made by combining while cooling in an ice bath, 2.33 g (0.03 mole) of a 40% aqueous solution of methylamine and 100 ml of methylene chloride. A second solution containing 3.08 g (0.015 mole) dichloroacetoxyacetyl chloride dissolved in 5 ml methylene chloride was slowly added to the first solution. The mixture was stirred in the ice bath for one half hour. After remaining at room temperature for one hour, it was refluxed for ten minutes and cooled again. The reaction product was water washed twice and dried over magnesium sulfate. It was decolorized with a decolorizing agent and charcoal. The solvent was removed by reduced pressure evaporation and oil pumped. A semi-solid consisting of 1.5 g (50% yield) of N-methyl dichloroacetoxyacetamide was obtained. The structure was confirmed by infrared spectraphotometric analysis (IR).

EXAMPLE 2

Preparation of 2,2-dimethyl-3-dichloroacetoxyacetyl oxazolidine (Compound No. 9)

A solution was made by combining while cooling in an ice bath, 1.51 g (0.015 mole) of 2,2-dimethyloxazolidine, 1.6 g (0.015 mole) of triethylamine, and 100 ml of methylene chloride. A second solution containing 3.08 g (0.015 mole) of dichloroacetoxyacetyl chloride dissolved in 10 ml of methylene chloride was added dropwise to the first solution. The mixture was stirred in the ice bath for ten minutes. After refluxing for one hour, it was allowed to cool to room temperature. The reaction product was water washed twice and dried over magnesium sulfate. It was decolorized with a decolorizing agent and charcoal. The solvent was removed by reduced pressure evaporation leaving 2.8 g (69% yield) of 2,2-dimethyl-3-dichloroacetoxyacetyloxazolidine. The structure was confirmed by IR.

EXAMPLE 3

Preparation of N,N-diallyl-2,3-dibromopropionyloxyacetamide (Compound No. 16)

A solution of 2.33 g (0.015 mole) N,N-diallyl glycolamide and 1.5 g (0.015 mole) triethylamine was dissolved in 100 ml methylene chloride in a reaction flask. After placing the flask in an ice bath, 3.76 g (0.015 mole) of 2,3-dibromopropionyl chloride was slowly added to the solution. The flask was removed from the ice bath and the solution was stirred for one hour at room temperature. It was refluxed for one hour and cooled again. Two water washings were followed by drying with magnesium sulfate. The mixture was decolorized with a decolorizing agent and charcoal. The solvent was removed by reduced pressure evaporation and oil pumped to produce 2.7 g (66.8% yield) of the product N,N-diallyl-2,3-dibromopropionyloxyacetamide. The structure was confirmed by IR and the nuclear magnetic resonance spectrum (NMR).

EXAMPLE 4

Preparation of N-1,1-dimethylpropynyl chloroacetoxyacetamide (Compound No. 18)

The reactant chloroacetoxyacetyl chloride was prepared by the following intermediate step. A solution was made by mixing 127 grams (g) of chloroacetyl chloride and 57 g of glycolic acid. This mixture was refluxed for two hours. When the evolution of hydrogen chloride ceased the mixture was stripped. The residue was then refluxed for two hours with thionyl chloride. The product was distilled under a water aspirator and fractioned between 105° and 115° C. A yield of 48 g (37%) was obtained. The structure was confirmed by IR, NMR, and mass spectrometry.

Triethylamine (5.50 g or 0.05 mole) and 3-amino-3-methyl-1-butyne (4.2 g or 0.05 mole) were dissolved in 100 milliliters (ml) of benzene. The reaction flask was cooled in an ice bath during the gradual addition of 8.55 g (0.05 mole) of the chloroacetoxyacetyl chloride. A precipitate formed immediately. The mixture was refluxed for one-half hour and allowed to stand overnight at room temperature. The reaction product was water washed three times and dried over magnesium sulfate. It was decolorized with a decolorizing agent and charcoal. After filtering and stripping, 8 g (73% yield) of N-1,1-dimethylpropynyl chloroacetoxyacetamide was obtained. The structure was confirmed by IR and NMR.

TABLE I

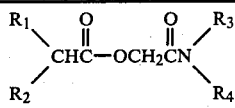

| Compound Number | $R_1$ | $R_2$ | $R_3$ | $R_4$ | Chemical Name |
|---|---|---|---|---|---|
| 1 | Cl | H | H | $-CHCH_2CH_3$ with $CH_3$ | N-sec-butyl chloroacetoxy-acetamide |
| 2 | Cl | Cl | H | $-CH_3$ | N-methyl dichloroacetoxy-acetamide |
| 3 | Cl | H | H | $-C(CH_3)_3$ | N-t-butyl chloroacetoxy-acetamide |
| 4 | Cl | Cl | H | $-C(CH_3)_3$ | N-t-butyl dichloroacetoxy-acetamide |

TABLE I-continued $$\underset{R_2}{\overset{R_1}{\diagdown}}CHC\underset{\parallel}{\overset{O}{\parallel}}-OCH_2C\underset{\parallel}{\overset{O}{\parallel}}N\underset{R_4}{\overset{R_3}{\diagup}}$$

| Compound Number | $R_1$ | $R_2$ | $R_3$ | $R_4$ | Chemical Name |
|---|---|---|---|---|---|
| 5 | Cl | H | H | $-\underset{CH_3}{\overset{CH_3}{\underset{|}{\overset{|}{C}}}}C_2H_5$ | N-t-pentyl chloroacetoxy acetamide |
| 6 | Cl | H | $-(CH_2)_2CH_3$ | $-(CH_2)_2CH_3$ | N,N-dipropyl chloroacetoxy-acetamide |
| 7 | Cl | Cl | $-(CH_2)_5-$ | | N,N-pentamethylene dichloro-acetoxyacetamide |
| 8 | Cl | H | $-CH_2CH_2OC(CH_3)_2-$ | | 2,2-dimethyl-3-chloro-acetoxyacetyloxazolidine |
| 9 | Cl | Cl | $-CH_2CH_2OC(CH_3)_2-$ | | 2,2-dimethyl-3-dichloro-acetoxyacetyloxazolidine |
| 10 | Cl | H | $-CH_2CH(CH_3)OC(CH_3)_2-$ | | 2,2,5-trimethyl-3-chloro-acetoxyacetyloxazolidine |
| 11 | Cl | Cl | $-CH_2CH(CH_3)OC(CH_3)_2-$ | | 2,2,5-trimethyl-3-dichloro acetoxyacetyl-oxazolidine |
| 12 | Cl | H | $-CH(C_2H_5)CH_2OC(CH_3)_2-$ | | 2,2,-dimethyl-4-ethyl-3-chloroacetoxyacetyl-oxazolidine |
| 13 | Cl | Cl | $-CH(C_2H_5)CH_2OC(CH_3)_2-$ | | 2,2-dimethyl-4-ethyl-3-dichloroacetoxyacetyl oxazolidine |
| 14 | Cl | H | $-CH_2CH=CH_2$ | $-CH_2CH=CH_2$ | N,N-diallyl chloroacetoxy-acetamide |
| 15 | Cl | H | $-CH=C(CN)_2$ | $-CH_2CH=CH_2$ | N-allyl-N-methylene malononitrile chloro-acetoxy acetamide |
| 16 | $CH_2Br$ | Br | $-CH_2CH=CH_2$ | $-CH_2CH=CH_2$ | N,N-diallyl 2,3-dibromo-propionyloxyacetamide |
| 17 | Cl | H | H | $-\underset{CH_3}{\overset{CH_3}{\underset{|}{\overset{|}{C}}}}-C\equiv CH$ | N-1,1-dimethylpropynyl chloroacetoxyacetamide |
| 18 | Cl | Cl | H | $-\underset{CH_3}{\overset{CH_3}{\underset{|}{\overset{|}{C}}}}-C\equiv CH$ | N-1,1-dimethyl propynyl dichloroacetoxyacetamide |
| 19 | Cl | Cl | H | m-chlorophenyl | N-(m-chlorophenyl)-dichloro-acetoxyacetamide |
| 20 | Cl | H | H | 2,6-diethylphenyl | N-(2,6-diethylphenyl)-chloroacetoxyacetamide |

[1] Structures of each compound were confirmed by either IR, NRM, or mass spectrometry.

TESTING

Stock solutions of herbicide were prepared. One of these included two dilutions of S-propyl dipropylthiocarbamate, Vernam ® 6E. The solution was made by diluting 1000 mg of Vernam in 100 ml of water so that 3 ml when applied to a flat is equivalent to 6 lb/A (6.72 k/ha) preplant incorporation (PPI), and 2.5 ml is equivalent to 5 lb/A (5.6 k/ha) PPI.

A second herbicide solution was prepared by diluting 2667 mg of S-ethyl N,N-dipropyl thiocarbamate, Eptam ® in 500 ml of water so that 5 ml when applied to a flat is equivalent to 5 lb/A (5.6 k/ha) PPI.

A third herbicide solution was prepared by diluting 667 mg of S-ethyl diisobutyl thiocarbamate, Sutan ®, in 125 ml of water so that 5 ml when applied to a flat is equivalent to 5 lb/A (5.6 k/ha) PPI.

The antidote compounds were prepared by dissolving 95 mg of each compound in 15 ml of acetone so that 1.5 ml applied in-furrow (IF) to a flat was equivalent to 5 lb/A (5.6 k/ha). For pre-plant incorporation 60 mg of each candidate was dissolved in 15 ml of acetone so that 5 ml applied to a flat was equivalent to 5 lb/A (5.6 k/ha). Proportional dilutions of these stock solutions were also prepared.

All of the soil used in the tests described herein was loamy sand soil treated with 50 parts per million (ppm) each of cis-N[(trichloromethyl)thio]-4-cyclohexane-1,2-dicarboximide, a fungicide known as captan, and an 18-18-18 fertilizer which contains 18% by weight equivalent each of nitrogen, phosphorus pentoxide, and potassium oxide.

For the pre-plant incorporation method the herbicide and the antidote of each test group were incorporated into sandy loam soil as a tank mix using a five gallon rotary mixer. Control flats used for injury rating comparisons contained only the herbicide treated soil.

For in-furrow antidote applications planting flats were filled with sandy loam soil treated by PPI of the herbicide. A one pint sample of soil removed from each flat was retained to cover the seeds after treatment. After leveling and furrowing the soil, seeds of the crop or weed species were planted ½ inch deep. Each flat was divided in half by a wooden barrier. A stock solution of the antidote was atomized directly onto the exposed seeds and soil in the open furrows of one half of the flat. The other half of the flat provided the untreated herbicide control group. The seeds were then covered with the previously removed soil. The untreated sections of flats containing identical herbicide concentrations were compared for observed differences which would indicate lateral movement of the antidote through the soil.

The treated crops initially screened for diminution of herbicidal injury were corn, soybeans, wheat, cotton, barley, rice and milo. Those crops which showed a substantial reduction in injury were further tested at reduced rates of the antidotally effective compounds. The herbicides and antidote compounds were then screened on at least two weed species. The weed species tested for control included watergrass (*Echinochloa crusgalli*), foxtail (*Setaria viridis*), wild oat (*Avena fatua*), yellow nutsedge (*Cyperus esculentus*) and Johnsongrass (*Sorghum halepense*).

The flats were placed on greenhouse benches where temperature was maintained between 70° and 90° F. (21.1° to 50° C.). The soil was watered by sprinkling as needed to assure good plant growth.

The effectiveness of the antidote was determined by comparing the crop and weed species treated at each level of concentration to the untreated species.

Injury ratings were taken at two and four week intervals after soil treatment and seeding. Table II discloses the results of these tests on crops. Table III summarizes the results on weeds.

KEY TO TABLES II AND III

Application Methods:
 (1) Antidotes
  IF = In-furrow
  PPI = Pre-plant incorporation (tank mix)
  PES = Pre-emergence Surface Spray
  ST = Seed Treatment
 (2) Herbicides
  PPI except where noted by an asterisk (*). In that case, both antidote and herbicide are applied PES.

Herbicides:
VERNAM® = S-propyl dipropylthiocarbamate, U.S. Pat. No. 2,913,327.
EPTAM® = S-ethyl N,N-dipropylthiocarbamate, U.S. Pat. No. 2,913,327.
SUTAN® = S-ethyl diisobutylthiocarbamate, U.S. Pat. No. 2,913,327.

U = antidotally untreated
T = antidotally treated
— = no change

TABLE II

Effectiveness of Herbicidal Antidotes

| Antidote | | Herbicide | | % Crop Injury | | | | | | | | | | | | |
|---|---|---|---|---|---|---|---|---|---|---|---|---|---|---|---|---|
| Cmpd. | Rate | Meth- | | Rate | Milo | | Wheat | | Rice | | Barley | | Cotton | | Corn | | Soybean | |
| No. | lb/A | od | Name | lb/A | U | T | U | T | U | T | U | T | U | T | U | T | U | T |
| 1 | 5.00 | IF | VERNAM | 1.00 | 100 | — | 97 | — | 100 | — | 97 | — | | | | | | |
| | 5.00 | IF | VERNAM | 5.00 | | | | | | | | | 80 | — | 65 | — | 5 | — |
| | 5.00 | PPI | VERNAM | 6.00 | | | | | | | | | | | | | 50 | 35 |
| | 2.50 | PPI | VERNAM | 6.00 | | | | | | | | | | | | | 50 | 40 |
| | 2.00 | PPI | VERNAM | 6.00 | | | | | | | | | | | | | 60 | 50 |
| | 1.00 | PPI | VERNAM | 6.00 | | | | | | | | | | | | | 50 | 40 |
| | 0.50 | PPI | VERNAM | 6.00 | | | | | | | | | | | | | 60 | 40 |
| | 5.00 | IF | VERNAM | 6.00 | | | | | | | | | | | | | 40 | 80 |
| | 1.00 | PPI | VERNAM | 6.00 | | | | | | | | | | | | | 60 | — |
| 2 | 5.00 | IF | VERNAM | 1.00 | 100 | — | 85 | — | 95 | — | 55 | 30 | 50 | 40 | | | | |
| | 5.00 | IF | VERNAM | 6.00 | | | | | | | | | | | 95 | 0 | 60 | — |
| | 5.00 | IF | VERNAM | 1.70 | | | | | | | 75 | 30 | | | | | | |
| | 1.00 | IF | VERNAM | 1.70 | | | | | | | 75 | — | | | | | | |
| 3 | 5.00 | IF | VERNAM | 1.00 | 95 | — | 70 | — | 95 | — | 50 | — | 70 | — | | | | |
| | 5.00 | IF | VERNAM | 6.00 | | | | | | | | | | | 70 | 0 | 55 | 40 |
| | 5.00 | IF | VERNAM | 5.00 | | | | | | | | | | | | | 40 | — |
| | 1.00 | IF | VERNAM | 5.00 | | | | | | | | | | | | | 40 | 10 |
| | 5.00 | PPI | EPTAM | 5.00 | | | | | | | | | | | 70 | 0 | | |
| | 0.50 | PPI | EPTAM | 5.00 | | | | | | | | | | | 70 | 40 | | |
| 4 | 5.00 | IF | VERNAM | 1.00 | 100 | — | 77 | — | 87 | — | 82 | — | 50 | 10 | | | | |
| | 5.00 | IF | VERNAM | 6.00 | | | | | | | | | | | 90 | 70 | 60 | 70 |
| | 5.00 | PPI | VERNAM | 6.00 | | | | | | | | | | | | | 50 | — |
| | 2.50 | PPI | VERNAM | 6.00 | | | | | | | | | | | | | 50 | — |
| | 1.00 | PPI | VERNAM | 6.00 | | | | | | | | | | | | | 50 | — |
| | 0.50 | PPI | VERNAM | 6.00 | | | | | | | | | | | | | 50 | — |
| | 5.00 | PPI | SUTAN | 5.00 | | | | | | | | | 30 | — | | | | |
| | 1.00 | PPI | SUTAN | 5.00 | | | | | | | | | 30 | — | | | | |
| 5 | 5.00 | IF | VERNAM | 1.00 | 95 | — | 70 | — | 95 | 100 | 50 | 70 | 70 | — | | | | |
| | 5.00 | IF | VERNAM | 6.00 | | | | | | | | | | | 70 | 30 | 55 | 100 |
| | 5.00 | PPI | VERNAM | 1.00 | | | 75 | — | 100 | — | 75 | — | | | | | | |
| | 5.00 | PPI | VERNAM | 6.00 | | | | | | | | | | | | | 50 | — |
| | 2.50 | PPI | VERNAM | 6.00 | | | | | | | | | | | | | 50 | — |
| | 1.00 | PPI | VERNAM | 1.00 | | | 75 | — | 100 | — | 75 | — | | | | | | |
| | 1.00 | PPI | VERNAM | 6.00 | | | | | | | | | | | | | 50 | — |
| | 2.00 | PPI | VERNAM | 6.00 | | | | | | | | | | | | | 60 | — |
| | 1.00 | PPI | VERNAM | 6.00 | | | | | | | | | | | | | 60 | — |

TABLE II-continued
Effectiveness of Herbicidal Antidotes

| Antidote | | Herbicide | | % Crop Injury | | | | | | | | | | | | | |
|---|---|---|---|---|---|---|---|---|---|---|---|---|---|---|---|---|---|
| Cmpd. No. | Rate lb/A | Method | Name | Rate lb/A | Milo U | Milo T | Wheat U | Wheat T | Rice U | Rice T | Barley U | Barley T | Cotton U | Cotton T | Corn U | Corn T | Soybean U | Soybean T |
| | 0.50 | PPI | VERNAM | 6.00 | | | | | | | | | | | | | 60 | — |
| | 5.00 | PPI | EPTAM | 5.00 | | | | | | | | | | | 70 | 0 | | |
| | 0.50 | PPI | EPTAM | 5.00 | | | | | | | | | | | 70 | 60 | | |
| 6 | 5.00 | IF | VERNAM | 1.00 | 100 | — | 85 | — | 95 | — | 55 | 80 | 50 | 40 | | | | |
| | 5.00 | IF | VERNAM | 6.00 | | | | | | | | | | | 95 | — | 60 | 40 |
| | 5.00 | PPI | VERNAM | 1.00 | | | 75 | 100 | | | 75 | — | | | | | | |
| | 1.00 | PPI | VERNAM | 1.00 | | | 75 | — | | | 75 | — | | | | | | |
| 7 | 5.00 | IF | VERNAM | 1.00 | 100 | — | 75 | — | 95 | — | 98 | — | | | | | | |
| | 5.00 | IF | VERNAM | 5.00 | | | | | | | | | 85 | — | 50 | 30 | 60 | 60 |
| 8 | 5.00 | IF | VERNAM | 1.00 | 100 | — | 75 | — | 95 | — | 70 | — | 70 | 80 | | | | |
| | 5.00 | IF | VERNAM | 6.00 | | | | | | | | | | | 90 | 60 | 80 | 70 |
| | 5.00 | PPI | SUTAN | 5.00 | | | | | | | | | 30 | 55 | | | | |
| | 1.00 | PPI | SUTAN | 5.00 | | | | | | | | | 30 | 40 | | | | |
| 9 | 5.00 | IF | VERNAM | 1.00 | 100 | — | 75 | — | 95 | 70 | 70 | 60 | 70 | — | | | | |
| | 5.00 | IF | VERNAM | 6.00 | | | | | | | | | | | 90 | 0 | 80 | 90 |
| | 5.00 | PPI | VERNAM | 6.00 | | | | | | | | | | | | | 50 | — |
| | 2.50 | PPI | VERNAM | 6.00 | | | | | | | | | | | | | 50 | — |
| | 1.00 | PPI | VERNAM | 6.00 | | | | | | | | | | | | | 50 | — |
| | 0.50 | PPI | VERNAM | 6.00 | | | | | | | | | | | | | 60 | — |
| | 5.00 | PPI | EPTAM | 5.00 | | | | | | | | | | | 70 | 0 | | |
| | 0.50 | PPI | EPTAM | 5.00 | | | | | | | | | | | 70 | 0 | | |
| 10 | 5.00 | IF | VERNAM | 1.00 | 100 | 70 | 75 | 60 | 95 | 100 | 70 | 60 | 70 | — | | | | |
| | 5.00 | IF | VERNAM | 6.00 | | | | | | | | | | | 90 | 50 | 80 | — |
| | 5.00 | PPI | VERNAM | 1.00 | | | | | 100 | — | | | | | | | | |
| | 1.00 | PPI | VERNAM | 1.00 | | | | | 100 | — | | | | | | | | |
| 11 | 5.00 | IF | VERNAM | 1.00 | 100 | — | 75 | — | 95 | — | 70 | 50 | 70 | 60 | | | | |
| | 5.00 | IF | VERNAM | 6.00 | | | | | | | | | | | 90 | 0 | 80 | — |
| | 5.00 | IF | VERNAM | 1.25 | | | | | | | 70 | 50 | | | | | | |
| | 1.00 | IF | VERNAM | 1.25 | | | | | | | 70 | — | | | | | | |
| | 5.00 | PPI | EPTAM | 5.00 | | | | | | | | | | | 70 | 0 | | |
| | 0.50 | PPI | EPTAM | 5.00 | | | | | | | | | | | 70 | 0 | | |
| | 5.00 | PPI | SUTAN | 5.00 | | | | | | | | | 30 | — | | | | |
| | 1.00 | PPI | SUTAN | 5.00 | | | | | | | | | 30 | 60 | | | | |
| 12 | 5.00 | IF | VERNAM | 1.00 | 100 | — | 75 | — | 95 | 100 | 70 | — | 70 | — | | | | |
| | 5.00 | IF | VERNAM | 6.00 | | | | | | | | | | | 90 | — | 80 | 90 |
| | 5.00 | PPI | VERNAM | 1.00 | | | | | 100 | — | | | | | | | | |
| | 2.00 | PPI | VERNAM | 6.00 | | | | | | | | | | | | | 60 | — |
| | 1.00 | PPI | VERNAM | 6.00 | | | | | | | | | | | | | 60 | — |
| | 0.50 | PPI | VERNAM | 6.00 | | | | | | | | | | | | | 60 | — |
| | 1.00 | PPI | VERNAM | 1.00 | | | | | 100 | — | | | | | | | | |
| 13 | 5.00 | IF | VERNAM | 1.00 | 100 | — | 75 | 60 | 95 | — | 70 | 60 | 70 | — | | | | |
| | 5.00 | IF | VERNAM | 6.00 | | | | | | | | | | | 90 | 0 | 80 | 95 |
| | 5.00 | PPI | VERNAM | 6.00 | | | | | | | | | | | | | 50 | — |
| | 2.50 | PPI | VERNAM | 6.00 | | | | | | | | | | | | | 50 | 40 |
| | 2.00 | PPI | VERNAM | 6.00 | | | | | | | | | | | | | 60 | — |
| | 1.00 | PPI | VERNAM | 6.00 | | | | | | | | | | | | | 50 | — |
| | 1.00 | PPI | VERNAM | 6.00 | | | | | | | | | | | | | 60 | — |
| | 0.50 | PPI | VERNAM | 6.00 | | | | | | | | | | | | | 60 | — |
| | 5.00 | PPI | EPTAM | 5.00 | | | | | | | | | | | 70 | 0 | | |
| | 0.50 | PPI | EPTAM | 5.00 | | | | | | | | | | | 70 | 50 | | |
| 14 | 5.00 | IF | VERNAM | 1.00 | 100 | — | 75 | — | 95 | — | 98 | — | | | | | | |
| | 5.00 | IF | VERNAM | 5.00 | | | | | | | | | 85 | — | 50 | 40 | 60 | 30 |
| | 2.00 | PPI | VERNAM | 6.00 | | | | | | | | | | | | | 50 | 20 |
| | 1.00 | PPI | VERNAM | 6.00 | | | | | | | | | | | | | 50 | 30 |
| | 0.50 | PPI | VERNAM | 6.00 | | | | | | | | | | | | | 50 | — |
| | 0.005 | ST | VERNAM | 6.00 | | | | | | | | | | | | | 30 | 70 |
| | 0.0025 | ST | VERNAM | 6.00 | | | | | | | | | | | | | 30 | 0 |
| | 0.00125 | ST | VERNAM | 6.00 | | | | | | | | | | | | | 30 | 25 |
| | 2.00 | PES | VERNAM | 6.00* | | | | | | | | | | | | | 30 | 10 |
| | 1.00 | PES | VERNAM | 6.00* | | | | | | | | | | | | | 30 | — |
| | 0.50 | PES | VERNAM | 6.00* | | | | | | | | | | | | | 30 | 15 |
| | 5.00 | PPI | EPTAM | 5.00 | | | | | | | | | | | 70 | 75 | | |
| | 0.50 | PPI | EPTAM | 5.00 | | | | | | | | | | | 70 | 60 | | |
| 15 | 5.00 | IF | VERNAM | 1.00 | 95 | — | 75 | — | 95 | — | 50 | — | 70 | 20 | | | | |
| | 5.00 | IF | VERNAM | 6.00 | | | | | | | | | | | 90 | — | 60 | 70 |
| 16 | 5.00 | IF | VERNAM | 1.00 | 100 | — | 97 | — | 100 | — | 97 | — | | | | | | |
| | 5.00 | IF | VERNAM | 5.00 | | | | | | | | | 80 | — | 65 | — | 5 | — |
| | 5.00 | PPI | VERNAM | 6.00 | | | | | | | | | | | | | 50 | 40 |
| | 2.50 | PPI | VERNAM | 6.00 | | | | | | | | | | | | | 50 | 20 |
| | 1.00 | PPI | VERNAM | 6.00 | | | | | | | | | | | | | 50 | — |
| | 5.00 | IF | VERNAM | 6.00 | | | | | | | | | | | | | 40 | 80 |
| | 2.00 | PPI | VERNAM | 6.00 | | | | | | | | | | | | | 60 | 45 |
| | 1.00 | PPI | VERNAM | 6.00 | | | | | | | | | | | | | 60 | — |
| | 0.50 | PPI | VERNAM | 6.00 | | | | | | | | | | | | | 60 | — |
| 17 | 5.00 | IF | VERNAM | 1.00 | 95 | 75 | 90 | 75 | 90 | — | 90 | 80 | | | | | | |
| | 5.00 | IF | VERNAM | 5.00 | | | | | | | | | 95 | — | 90 | 0 | 40 | 95 |
| | 5.00 | PPI | VERNAM | 6.00 | | | | | | | | | | | | | 50 | — |

TABLE II-continued

Effectiveness of Herbicidal Antidotes

| Antidote | | Herbicide | | % Crop Injury | | | | | | | | | | | | | |
|---|---|---|---|---|---|---|---|---|---|---|---|---|---|---|---|---|---|
| Cmpd. | Rate | Meth- | | Rate | Milo | | Wheat | | Rice | | Barley | | Cotton | | Corn | | Soybean |
| No. | lb/A | od | Name | lb/A | U | T | U | T | U | T | U | T | U | T | U | T | U | T |
|  | 2.50 | PPI | VERNAM | 6.00 | | | | | | | | | | | | | 50 | 40 |
|  | 2.00 | PPI | VERNAM | 6.00 | | | | | | | | | | | | | 60 | — |
|  | 1.00 | PPI | VERNAM | 6.00 | | | | | | | | | | | | | 60 | — |
|  | 1.00 | PPI | VERNAM | 6.00 | | | | | | | | | | | | | 50 | 30 |
|  | 0.50 | PPI | VERNAM | 6.00 | | | | | | | | | | | | | 60 | — |
| 18 | 5.00 | IF | VERNAM | 1.00 | 100 | — | 77 | — | 87 | — | 82 | 60 | 50 | 70 | | | | |
|  | 5.00 | IF | VERNAM | 6.00 | | | | | | | | | | | 90 | 10 | 60 | 80 |
|  | 5.00 | PPI | VERNAM | 6.00 | | | | | | | | | | | | | 50 | 40 |
|  | 2.50 | PPI | VERNAM | 6.00 | | | | | | | | | | | | | 50 | — |
|  | 2.00 | PPI | VERNAM | 6.00 | | | | | | | | | | | | | 60 | — |
|  | 1.00 | PPI | VERNAM | 6.00 | | | | | | | | | | | | | 50 | — |
|  | 1.00 | PPI | VERNAM | 6.00 | | | | | | | | | | | | | 60 | — |
|  | 0.50 | PPI | VERNAM | 6.00 | | | | | | | | | | | | | 60 | — |
|  | 5.00 | PPI | EPTAM | 5.00 | | | | | | | | | | | 70 | 0 | | |
|  | 0.50 | PPI | EPTAM | 5.00 | | | | | | | | | | | 70 | 30 | | |
|  | 5.00 | PPI | SUTAN | 5.00 | | | | | | | | | 30 | 40 | | | | |
|  | 1.00 | PPI | SUTAN | 5.00 | | | | | | | | | 30 | 40 | | | | |
| 19 | 5.00 | IF | VERNAM | 1.00 | 100 | — | 85 | 60 | 95 | — | 55 | — | 50 | 30 | | | | |
|  | 5.00 | IF | VERNAM | 6.00 | | | | | | | | | | | 95 | — | 60 | 40 |
|  | 5.00 | PPI | VERNAM | 1.00 | | | 75 | 30 | | | 75 | 30 | | | | | | |
|  | 1.00 | PPI | VERNAM | 1.00 | | | 75 | 40 | | | 75 | 30 | | | | | | |
| 20 | 5.00 | IF | VERNAM | 1.00 | 100 | — | 85 | — | 95 | | 55 | — | 50 | 40 | | | | |
|  | 5.00 | IF | VERNAM | 6.00 | | | | | | | | | | | 95 | 80 | 60 | 20 |
|  | 5.00 | IF | VERNAM | 6.00 | | | | | | | | | | | | | 50 | 40 |
|  | 1.00 | IF | VERNAM | 6.00 | | | | | | | | | | | | | 50 | — |

TABLE III

Effectiveness of Herbicidal Compositions

| Antidote | | | Herbicide | | % Weed Injury | | | | | | | | | |
|---|---|---|---|---|---|---|---|---|---|---|---|---|---|---|
| | | | | | Water-grass | | Foxtail | | Wild oat | | Yellow Nutsedge | | Johnson-grass | |
| Cmpd. | Rate | Meth- | | Rate | | | | | | | | | | |
| No. | lb/A | od | Name | lb/A | U | T | U | T | U | T | U | T | U | T |
| 1 | 5.00 | PPI | VERNAM | 6.00 | 100 | — | 100 | — | | | | | | |
|  | 2.50 | PPI | VERNAM | 6.00 | 100 | — | 100 | — | | | | | | |
|  | 1.00 | PPI | VERNAM | 6.00 | 100 | — | 100 | — | | | | | | |
|  | 2.00 | PPI | VERNAM | 6.00 | | | 100 | — | | | 100 | — | | |
|  | 1.00 | PPI | VERNAM | 6.00 | | | 100 | — | | | 100 | — | | |
|  | 0.50 | PPI | VERNAM | 6.00 | | | 100 | — | | | 100 | — | | |
| 2 | 5.00 | IF | VERNAM | 1.70 | 60 | — | 60 | — | | | | | | |
|  | 1.00 | IF | VERNAM | 1.70 | 60 | — | 60 | — | | | | | | |
|  | 5.00 | PPI | EPTAM | 5.00 | 95 | — | 95 | — | | | | | | |
|  | 0.50 | PPI | EPTAM | 5.00 | 95 | — | 95 | — | | | | | | |
| 3 | 5.00 | IF | VERNAM | 5.00 | 100 | — | 100 | — | | | | | | |
|  | 1.00 | IF | VERNAM | 5.00 | 100 | — | 100 | — | | | | | | |
|  | 5.00 | PPI | EPTAM | 5.00 | 95 | — | 95 | — | | | | | | |
|  | 0.50 | PPI | EPTAM | 5.00 | 95 | — | 95 | — | | | | | | |
| 4 | 5.00 | PPI | VERNAM | 6.00 | 100 | — | 100 | — | | | | | | |
|  | 2.50 | PPI | VERNAM | 6.00 | 100 | — | 100 | — | | | | | | |
|  | 1.00 | PPI | VERNAM | 6.00 | 100 | — | 100 | — | | | | | | |
|  | 2.00 | PPI | VERNAM | 6.00 | | | 100 | — | | | 100 | — | | |
|  | 1.00 | PPI | VERNAM | 6.00 | | | 100 | — | | | 100 | — | | |
|  | 0.50 | PPI | VERNAM | 6.00 | | | 100 | — | | | 100 | — | | |
|  | 5.00 | PPI | SUTAN | 5.00 | 95 | — | | | | | | | 95 | — |
|  | 1.00 | PPI | SUTAN | 5.00 | 95 | — | | | | | | | 95 | — |
| 5 | 5.00 | PPI | VERNAM | 6.00 | 100 | — | 100 | — | | | | | | |
|  | 2.50 | PPI | VERNAM | 6.00 | 100 | — | 100 | — | | | | | | |
|  | 1.00 | PPI | VERNAM | 6.00 | 100 | — | 100 | — | | | | | | |
|  | 2.00 | PPI | VERNAM | 6.00 | | | 100 | — | | | 100 | — | | |
|  | 1.00 | PPI | VERNAM | 6.00 | | | 100 | — | | | 100 | — | | |
|  | 0.50 | PPI | VERNAM | 6.00 | | | 100 | — | | | 100 | — | | |
|  | 5.00 | PPI | VERNAM | 1.00 | 100 | — | | | 100 | — | | | | |
|  | 5.00 | PPI | VERNAM | 1.00 | | | | | 100 | — | | | | |
|  | 1.00 | PPI | VERNAM | 1.00 | 100 | — | | | 100 | — | | | | |
|  | 1.00 | PPI | VERNAM | 1.00 | | | | | 100 | — | | | | |
|  | 5.00 | PPI | EPTAM | 5.00 | 95 | — | 95 | — | | | | | | |
|  | 0.50 | PPI | EPTAM | 5.00 | 95 | — | 95 | — | | | | | | |
| 8 | 5.00 | PPI | SUTAN | 5.00 | 95 | — | | | | | | | 95 | — |
|  | 1.00 | PPI | SUTAN | 5.00 | 95 | — | | | | | | | 95 | — |
| 9 | 5.00 | PPI | VERNAM | 6.00 | 100 | — | 100 | — | | | | | | |
|  | 2.50 | PPI | VERNAM | 6.00 | 100 | — | 100 | — | | | | | | |
|  | 1.00 | PPI | VERNAM | 6.00 | 100 | — | 100 | — | | | | | | |
|  | 2.00 | PPI | VERNAM | 6.00 | | | 100 | — | | | 100 | — | | |
|  | 1.00 | PPI | VERNAM | 6.00 | | | 100 | — | | | 100 | — | | |
|  | 0.50 | PPI | VERNAM | 6.00 | | | 100 | — | | | 100 | — | | |

TABLE III-continued
Effectiveness of Herbicidal Compositions

| | | | | | % Weed Injury | | | | | | | | |
|---|---|---|---|---|---|---|---|---|---|---|---|---|---|
| Antidote | | | Herbicide | | Water- | | | | | | Yellow | | Johnson- |
| Cmpd. | Rate | Meth- | | Rate | grass | | Foxtail | | Wild oat | | Nutsedge | | grass |
| No. | lb/A | od | Name | lb/A | U | T | U | T | U | T | U | T | U | T |
| | 5.00 | PPI | EPTAM | 5.00 | 95 | — | 95 | — | | | | | | |
| | 0.50 | PPI | EPTAM | 5.00 | 95 | — | 95 | — | | | | | | |
| 11 | 5.00 | IF | VERNAM | 1.25 | 90 | — | | | 100 | — | | | | |
| | 1.00 | IF | VERNAM | 1.25 | 90 | 50 | | | 100 | — | | | | |
| | 5.00 | PPI | EPTAM | 5.00 | 95 | — | 95 | — | | | | | | |
| | 0.50 | PPI | EPTAM | 5.00 | 95 | — | 95 | — | | | | | | |
| | 5.00 | PPI | SUTAN | 5.00 | 95 | — | | | | | | | 95 | — |
| | 1.00 | PPI | SUTAN | 5.00 | 95 | — | | | | | | | 95 | — |
| 12 | 2.00 | PPI | VERNAM | 6.00 | | | 100 | — | | | 100 | — | | |
| | 1.00 | PPI | VERNAM | 6.00 | | | 100 | — | | | 100 | — | | |
| | 0.50 | PPI | VERNAM | 6.00 | | | 100 | — | | | 100 | — | | |
| 13 | 5.00 | PPI | VERNAM | 6.00 | 100 | — | 100 | — | | | | | | |
| | 2.50 | PPI | VERNAM | 6.00 | 100 | — | 100 | — | | | | | | |
| | 1.00 | PPI | VERNAM | 6.00 | 100 | — | 100 | — | | | | | | |
| | 2.00 | PPI | VERNAM | 6.00 | | | 100 | — | | | 100 | — | | |
| | 1.00 | PPI | VERNAM | 6.00 | | | 100 | — | | | 100 | — | | |
| | 0.50 | PPI | VERNAM | 6.00 | | | 100 | — | | | 100 | — | | |
| | 5.00 | PPI | EPTAM | 5.00 | 95 | — | 95 | — | | | | | | |
| | 0.50 | PPI | EPTAM | 5.00 | 95 | — | 95 | — | | | | | | |
| 14 | 5.00 | PPI | EPTAM | 5.00 | 95 | — | 95 | — | | | | | | |
| | 0.50 | PPI | EPTAM | 5.00 | 95 | — | 95 | — | | | | | | |
| 16 | 5.00 | PPI | VERNAM | 6.00 | 100 | — | 100 | — | | | | | | |
| | 2.50 | PPI | VERNAM | 6.00 | 100 | — | 100 | — | | | | | | |
| | 1.00 | PPI | VERNAM | 6.00 | 100 | — | 100 | — | | | | | | |
| | 2.00 | PPI | VERNAM | 6.00 | | | 100 | — | | | 100 | — | | |
| | 1.00 | PPI | VERNAM | 6.00 | | | 100 | — | | | 100 | — | | |
| | 0.50 | PPI | VERNAM | 6.00 | | | 100 | — | | | 100 | — | | |
| 17 | 5.00 | PPI | VERNAM | 6.00 | 100 | — | 100 | — | | | | | | |
| | 2.50 | PPI | VERNAM | 6.00 | 100 | — | 100 | — | | | | | | |
| | 1.00 | PPI | VERNAM | 6.00 | 100 | — | 100 | — | | | | | | |
| | 2.00 | PPI | VERNAM | 6.00 | | | 100 | — | | | 100 | — | | |
| | 1.00 | PPI | VERNAM | 6.00 | | | 100 | — | | | 100 | — | | |
| | 0.50 | PPI | VERNAM | 6.00 | | | 100 | — | | | 100 | — | | |
| 18 | 5.00 | PPI | VERNAM | 6.00 | 100 | — | 100 | — | | | | | | |
| | 2.50 | PPI | VERNAM | 6.00 | 100 | — | 100 | — | | | | | | |
| | 1.00 | PPI | VERNAM | 6.00 | 100 | — | 100 | — | | | | | | |
| | 2.00 | PPI | VERNAM | 6.00 | | | 100 | — | | | 100 | — | | |
| | 1.00 | PPI | VERNAM | 6.00 | | | 100 | — | | | 100 | — | | |
| | 0.50 | PPI | VERNAM | 6.00 | | | 100 | — | | | 100 | — | | |
| | 5.00 | PPI | EPTAM | 5.00 | 95 | — | 95 | — | | | | | | |
| | 0.50 | PPI | EPTAM | 5.00 | 95 | — | 95 | — | | | | | | |
| | 5.00 | PPI | SUTAN | 5.00 | 95 | — | | | | | | | 95 | — |
| | 1.00 | PPI | SUTAN | 5.00 | 95 | — | | | | | | | 95 | — |
| 20 | 5.00 | IF | VERNAM | 6.00 | 100 | — | 100 | — | | | | | | |
| | 1.00 | IF | VERNAM | 6.00 | 100 | — | 100 | — | | | | | | |

The compounds of the present invention show good antidotal activity for the protection of a variety of crops, especially corn, from thiocarbamate herbicidal injury. Their use results in almost no loss of herbicidal effectiveness.

FORMULATIONS

The compounds and compositions can be formulated in the same manner in which herbicides are generally formulated. They may be applied either separately or combined with the herbicide as part of a two-part herbicidal system.

Although application may be made at any of the stages of growth previously discussed, the preferred methods of application are in-furrow and pre-plant incorporation.

The object of the formulation is to apply the compounds and compositions to the locus where control is desired by a convenient method. The "locus" may include soil, seeds, seedlings, and vegetation.

Formulations will generally contain several additives. Among these are some inert ingredients and diluent carriers such as organic solvents, water, oil and water, water in oil emulsions, carriers of dust and granules, and surface active, wetting, dispersing, and emulsifying agents.

Fertilizers, e.g., ammonium nitrate, urea and superphosphate, may also be added.

Aids to rooting and growth, e.g., compost, manure, humus, sand, etc., may likewise be added.

The formulations are commonly dusts, wettable powders, granules, solutions or emulsifiable concentrates.

Dusts are free-flowing powder compositions containing the herbicidal compound impregnated on a particulate carrier. The particle size of the carriers is usually in the approximate range of 30 to 50 microns. Examples of suitable carriers are talc, bentonite, diatomaceous earth, and pyrophyllite. Anti-caking and anti-static agents can be added, if desired. The composition generally contains up to 50% of active ingredient. Dusts, like liquid compositions, can be applied by sprays from boom and hand sprayers or airplanes.

Wettable powders are finely divided compositions comprising a particulate carrier impregnated with the herbicidal compound and additionally containing one or more surface active agents. The surface active agent promotes rapid dispersion of the powder in aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols, in which the alcohol groups are free, omega-substituted polyethylene glycols of relatively long chain length. A list of surface active agents suitable for use in agriculture formulations can be found in Wade Van Valkenburg, *Pesticide Formulations* (Marcel Dekker, Inc., N.Y., 1973) at pages 79–84.

Granules comprise the herbicidal composition impregnated on a particulate inert carrier having a particle size of about 1 to 2 millimeters in diameter. The granules can be made by spraying a solution of the active ingredient in a volatile solvent onto the granular carrier. Suitable carriers in preparation of granules include clay, vermiculite, sawdust, granular carbon, etc.

The herbicidal compositions can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate.

The compounds and compositions of this invention can also be applied by addition to irrigation water supplied to the field to be treated. This method of application permits the penetration of the compositions into the soil as the water is absorbed therein.

It is not necessary that the compounds and compositions be admixed with the soil particles. After application by the above discussed methods, they may be distributed below the surface to a depth of at least one-half inch by conventional means such as discing, dragging, or mixing.

What is claimed:

1. N-substituted haloacyloxyacetamide compounds corresponding to th following formula

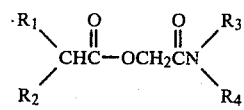

in which

R$_1$ is selected from the group consisting of chlorine and bromoethyl;

R$_2$ is selected from the group consisting of hydrogen, chlorine and bromine;

R$_3$ and R$_4$ together with the nitrogen atom to which they are attached form a 4–10 carbon alkyl substituted oxazolidine ring.

2. A compound according to claim 1 in which R$_1$ is chloro, R$_2$ is hydrogen, and R$_3$ and R$_4$ together with the nitrogen atom to which they are attached form 2,2,5-trimethyl-3-oxazolidine.

3. A compound according to claim 1 in which R$_1$ is chloro, R$_2$ is chloro, and R$_3$ and R$_4$ together with the nitrogen atom to which they are attached form a 4–10 carbon alkyl substituted oxazolidine ring.

4. A compound according to claim 3 in which the substituted oxazolidine ring is 2,2-dimethyl-3-oxazolidine.

5. A compound according to claim 3 in which the substituted oxazolidine ring is 2,2,5-trimethyl-3-oxazolidine.

6. A compound according to claim 3 in which the substituted oxazolidine ring is 2,2-dimethyl-4-ethyl-3-oxazolidine.

* * * * *